(12) United States Patent
Simonsen et al.

(10) Patent No.: US 6,540,672 B1
(45) Date of Patent: Apr. 1, 2003

(54) MEDICAL SYSTEM AND A METHOD OF CONTROLLING THE SYSTEM FOR USE BY A PATIENT FOR MEDICAL SELF TREATMENT

(75) Inventors: Jan Henning Simonsen, Struer (DK); Jens Ulrik Poulsen, Virum (DK); Kent Halfdan Rokkjaer, Holstebro (DK); Lars Hofmann Christensen, Jyllinge (DK); Søren Aasmul, Holte (DK); Steffen Iav, Brønshøj (DK)

(73) Assignee: Novo Nordisk A/s, Bagsvaerd (DK)

(*) Notice: Subject to any disclaimer, the term of this patent is extended or adjusted under 35 U.S.C. 154(b) by 0 days.

(21) Appl. No.: 09/450,193

(22) Filed: Nov. 29, 1999

Related U.S. Application Data
(60) Provisional application No. 60/111,721, filed on Dec. 9, 1998.

(51) Int. Cl.[7] .................................................. A61B 5/00
(52) U.S. Cl. ...................... 600/300; 128/903; 600/316
(58) Field of Search .......................... 604/187, 65, 503; 600/300, 316, 584, 533, 309, 583, 367; 710/72; 235/380; 607/32, 60; 128/897, 898, 903; 709/208, 209

(56) References Cited

U.S. PATENT DOCUMENTS

| | | | |
|---|---|---|---|
| 3,786,510 A | * | 1/1974 | Hodges ........................ 600/584 |
| 4,523,297 A | * | 6/1985 | Ugon et al. .................. 235/380 |
| 5,204,670 A | | 4/1993 | Stinton |
| 5,313,941 A | * | 5/1994 | Braig et al. .................. 600/216 |
| 5,371,687 A | * | 12/1994 | Holmes, II et al. ........... 710/72 |
| 5,536,249 A | * | 7/1996 | Castellano et al. ........... 604/65 |
| 5,549,117 A | * | 8/1996 | Tacklind et al. ............. 600/533 |
| 5,672,154 A | * | 9/1997 | Sillen et al. ................. 604/503 |
| 5,687,717 A | * | 11/1997 | Halpern et al. .............. 128/903 |
| 5,752,976 A | * | 5/1998 | Duffin et al. ................. 607/32 |
| 5,842,976 A | * | 12/1998 | Williamson ................. 600/300 |
| 6,363,416 B1 | * | 3/2002 | Naeimi et al. ............... 709/209 |

FOREIGN PATENT DOCUMENTS

WO    WO98/02086    1/1998

OTHER PUBLICATIONS

CA 1296068 C (Friesen EJ) Feb. 18, 1992 (abstract), World Patents Index (online), London, U.K., Derwent Publications, Ltd. (retrieved from: EPO WPI database DW9214, Accession No. 92–105121).

* cited by examiner

*Primary Examiner*—Eric F. Winakur
*Assistant Examiner*—David J. McCrosky
(74) *Attorney, Agent, or Firm*—Marc A. Began, Esq.; Richard W. Bosk, Esq.; Reza Green, Esq.

(57) ABSTRACT

This invention relates to an system for self treatment. The system consists of several portable modules where one of the modules is designated as a master module. The master module controls, supervises and monitors all the mutual information and data exchange between itself and the rest of the modules. The modules can e.g. consist of a BGM, a doser, an inhaler, a tablet dispenser and a storage container. The modules may be able to generate and store data which is transmitted to the master module if it is within range and active. If the master module is not within range, the data is kept locally in the module until the master module is available or a new master module is designated. The master module or another specific module can send the data to an external unit like a computer or database for further processing. A physician or an expert care-team can access the data in the database and give guidance to the patient on the basis of these processed data. This processing could also be done automatically by utilization of an expert system.

15 Claims, 11 Drawing Sheets

MEDICAL SYSTEM AND A METHOD OF CONTROLLING THE SYSTEM FOR USE BY A PATIENT FOR MEDICAL SELF TREATMENT

This application claims benefit of Ser. No. 60/111,721 filed Dec. 9, 1998.

This invention comprises a medical system and a method of controlling the system for use by a patient for medical self treatment.

For a number of years it has been possible to purchase various devices for the treatment of diabetes, e.g. for injecting insulin, for measuring blood sugar (such a device is referred to as BGM in the following), for withdrawing blood samples, and other accessories, the purpose of which is to enable the patient to nurse his disease discretely and with a high standard of safety.

Many diabetic patients are elderly people who can easily get insecure with respect to the medical equipment. It is very reassuring and therefore also very important that the user can have feedback from the system which confirms to the user that everything is OK right from the technical function of the system to the patient's physiological condition. This stretches out a psychological safety net under the patient, which contributes to improving the quality of life of patients having a disease such as diabetes.

Also many young people need to assure themselves that the equipment is in order, i.e. calibrated, powered, updated and otherwise ready to be operated.

One way of ensuring that you have all the things needed ready at hand is to build several of the necessary devices together into a single integral unit, see e.g. U.S. Pat. No. 5,536,249 and No. 5,593,390. This is not an ideal solution since such a multi-functional device is usually quite complex both with respect to manufacture and use. People need to be familiar, secure and confident with the use of a device for self-treatment which such an integral multi-functional device does not provide.

Another drawback of integrating several functions in one apparatus is that owing to the commercial outlets the manufacturer never integrates all possibilities, but just the most important ones, in order for it to be relevant to a sufficiently large group of users. The functions which are thus not integrated must be provided by means of separate apparatuses typically of different makes, which can easily create uncertainty as to whether the apparatuses work correctly together.

Additionally, the functionality and the individual devices of an integral multi-functional device are very hard if not impossible to update without updating everything else.

According to the invention the individual devices may be arranged for various respective functions relevant to the treatment of e.g. diabetes, such as: a lancet device, a body fluid analyser, one or more drug administration apparatuses for administering a predetermined dose of medication to the patient. Further, there is a number of other aids which the diabetic patient uses, e.g. test strips for the blood analyser, needles, napkins for wiping off blood, extra insulin cartridge, glucose tablets, waste containers, etc.

The object of the invention is to provide a method for effective monitoring of electronic data relevant to a plurality of apparatuses/units which are used by a patient for self-treatment of a disease, so that a greater level of safety, both functionally and emotionally, and an effective feedback to the patient are obtained.

This is achieved according to the invention in that the individual apparatuses are provided with electronic communications equipment so that the apparatuses—when in a state of mutual communication—frequently exchange information between them. Hereby a greater functional safety can be achieved and the total data capacity of the system can be increased, so that the feedback possibilities, e.g. of the system checking that every apparatus is OK and set up properly and of the patient be given a number of possible choices to choose from in a given situation, are increased.

More particularly, the invention relates to a method of controlling data information between a plurality of portable apparatuses for use by a patient for medical self treatment, the treatment including a first operation and at least a second operation, said portable apparatuses comprising a first apparatus for performing the first operation, and at least a second apparatus for performing the second operation, wherein each apparatus belonging to the medical self treatment has means for one or more of the following: storing, transmitting, receiving, processing and displaying information, an attempted data communication between said apparatuses is initiated on request, said communication being controlled by a functional master module, and designating said functional master module among at least two of said apparatuses.

The request can e.g. be initiated by a timer or other external events such as the patient performing an action. The invention provides the specialeffect that a patient need not bring along a large apparatus technically complicated in use in order to treat his disease, but that the apparatus may be divided into several smaller and simpler units capable of communicating mutually. The individual units may optionally be adapted to be interconnected mechanically, as disclosed in Danish Patent Application No. PA199800714.

According to the invention, all apparatuses need not be active for communication to be established between some of the apparatuses. This requires that all the apparatuses are adapted to a specific communications protocol, there being several options in this respect. For example, one of the units may be provided with program information of highest priority with respect to the control and monitoring of data communication between the individual apparatuses and being designated as the functional master module, where the program information of highest priority may either be activated in or transferred to the designated functional master module. The unit of highest priority may very well be turned off by the user or even be broken, because the apparatuses may be adapted to communicate directly with each other and perform storage of information, which is subsequently transmitted to the unit of highest priority when this is again in communication with another of the apparatuses.

Preferably a protocol where a number of potential master modules (unit of highest priority) is predefined. These predefined potential master modules are given a hierarchical priority and the potential master module with the highest priority among the activated and present potential master modules becomes the functional master module. This master module polls the other activated and present apparatuses for information.

In this way, when the user selects some of the apparatuses and takes them with him for a shorter or longer period of time, he still has a group/subset of apparatuses relevant to his self treatment which communicates/exchanges information with each other, where the designated functional master module is responsible for controlling the communication between the subset of apparatuses. The functional master module may receive and store/mirror all the information provided by/at the individual apparatuses for backup purposes, and for processing and collecting of information and an easier update with an overall master module (the one with the highest hierarchical priority), since it contains a mirror of all the information/data. Additionally the functional master module is responsible for controlling the transmission of relevant data, e.g. received from another apparatus, to the appropriate apparatus(es).

If the functional master module becomes unavailable, the individual apparatuses may just store the information locally until the master module becomes available or initiate the designation of a new functional master module, i.e. the one with the highest available priority.

U.S. Pat. No. 5,204,670 discloses a system for monitoring and identification which has a master module which transmits information collected from different sensors to a central system for further processing. It mentions the possibility of using software and hardware modules to implement a flexible system, but once the selection of modules has been made, the system and configuration are static.

WO 98/02086 discloses an inspection and measurement system where a simple terminal is installed in a house of a patient with a data collector and where a central control unit collects information from a number of terminals (located in different houses).

None of the two specifications discloses a system where a portable set, e.g. subset, of apparatuses can communicate and exchange information, relevant to a self treatment of a disease, with each other, and thus they do not provide a flexible system with greater functional safety and better feedback possibilities arising from the mutual exchange of information between the apparatuses.

Alternatively, other communications protocols may be implemented such as:

A protocol for a self-organizing network where every apparatus retransmits all the received information until the apparatus or apparatuses that the information was meant for receive it. In this way every apparatus functions as a relay station or as a functional master module and a temporary storage of transmitted information. This structure is especially useful when the configuration of the network is not known or when the configuration of the network changes in an unpredictable manner. Another feature of a network of this kind is that a maximal number of redundant transmission paths with a buffer are created so that the system can transmit information to apparatuses that were not available when the information was transmitted.

A protocol where all the apparatuses transmits their information without any supervision of any kind. The apparatuses themselves have to decide what information is relevant for them.

One single unit/apparatus, e.g. the unit of highest priority/overall master module, is preferably adapted to communicate with a larger central communication center/external system which may contain a patient database. Such further use of the invention is known e.g. from U.S. Pat. No. 5,204,670 or WO 98/02086, which, cannot however, offer the patient the flexible and safe use of a set of different apparatuses with mutual communication according to the invention which together are used in the treatment of a disease.

The apparatuses according to the invention communicate and process information such as: amount of medication, type of medication, the concentration of relevant substances in the body e.g. body fluid level/concentration, time stamp, amount of food (e.g. amount or units of carbohydrate), measurement of physical activity, notification (e.g. alert and warning) to the patient, body characteristics (e.g. weight, blood pressure etc.) and inventory logistics. This ensures that relevant information, for e.g. a drug administration system like a doser, i.e. number of units of insulin, insulin type and time and date for administering, can automatically be stored, displayed, received and transmitted to and from all the relevant apparatuses. The doser could also receive information regarding a predetermined number of units of insulin to be administered and automatically set the amount of medication to be administered by electromechanical means. In this way elderly and handicapped people do not have to set the relevant amount of medication themselves but just activate the doser.

Other types of drug administration systems like an inhaler adapted to administer a dose of medication in an air stream or a tablet dispenser may be included instead or in combination with the doser. The inhaler and/or tablet dispenser may also communicate with the other units for relevant information like the doser according to the invention.

Additionally, different types and makes of apparatuses may be provided like e.g. a simpler backup doser, which for a shorter period replaces one of the normally used dosers e.g. temporarily out of order, a special doser particularly suited for sports, e.g. by being more robust, or apparatuses which have different color schemes and/or design (e.g. for kids, etc.).

It is especially useful to transmit the data from all apparatuses to the apparatus responsible for communicating with external systems for safe keeping, calibration, synchronisation and updating of data and possible transmission to e.g. an external unit like a PC or database for further data acquisition, storage and processing. In this way the patient, a physician or an expert care-team can obtain the behavior over time of the patient, a a check for compliance to a diet or treatment given to the patient by a physician or an expert care-team can be made. This could also be done automatically.

Additionally, it is also possible for the patient to manually input information about the treatment. This information may be historic information as well as information about a future scheme (behavioral pattern) e.g. planned physical exercise, administering of insulin, intake of food and other medications. This information may be collected and thus serve as an electronic diabetes diary or may be used to notify the patient through the receiving means as to whether the planned actions are dangerous or not.

It is evident that since the apparatuses are to be carried by the patient, there is a potential lack of space for an advanced input device e.g. a keyboard. Therefore, information which cannot be input on a standardized form e.g. personal comments on the treatment is types into the apparatus by the patient using a simple input device once and can subsequently be chosen from a list if needed again.

The patient can further receive recommended amounts of medication, exercise, food, etc. from a physician, from an expert-team or automatically.

Additionally, since only one unit provides a link between the system and any outside systems, the great advantage that only one unit needs to be updated with respect to external communications protocols, etc. if the outside systems specifications change, is achieved.

All the apparatuses of the system may exchange information so that every apparatus (or at least every apparatus within range) is updated with the total information, so that every bit of information is mirrored for better safety and backup, but preferably one particular apparatus is still the link to any outside systems. This demands a greater amount of total memory capacity for the system, but with the ever decreasing price (and size) of memory modules that may be irrelevant.

Alternatively, the individual apparatuses are just updated with information relevant to them and send their information to one overall or one temporarily unit of highest priority, i.e. functional master module.

The invention also relates to a medical system for use by a patient for medical self treatment, the treatment including a first operation and at least a second operation, the apparatus comprising a first apparatus for performing the first operation and a second apparatus for performing the second operation, wherein each apparatus comprises means for storing, processing and/or displaying information, and comprises means for transmitting and receiving information so that each apparatus is able to exchange data with any of the other apparatuses belonging to the self treatment, at least two of said apparatuses being a potential functional master module, one of said potential functional master module being designated as the functional master module, and that said functional master module is adapted to control an attempted data communication, initiated on request, between said apparatuses.

For a BGM according to an embodiment of the invention the relevant information could be the time and date for measurement, measured level/concentration of blood glucose that could be stored or transmitted to another apparatus.

For a doser according to an embodiment of the invention the relevant information could be the type of medication (e.g. long acting or short acting insulin), number of units of insulin to be administered and the time and date of the administering. This information could either be set mutually by the patient or remotely by a physician, an expert care-team or automatically.

For an insulin according to an embodiment of the invention the relevant information could be the type of medication, the number of units of medication to be administered and the time and date of the administering. This information could either be set manually by the patient or remotely by a physician, an expert care-team or automatically.

For a storage container according to an embodiment of the invention the relevant information could be used to keep track of the contents of the container so that every time an object (e.g. cartridge, needle, etc.) is used, the storage container will update the inventory list. This list could be transferred to an unit of highest priority immediately or later, which could in turn update the patient's total holdings of objects, so that the system could notify the patient when he should order a new stock of objects. The ordering could also be done automatically by the system if the inventory list is transferred to an external unit, which greatly improves the confidence, comfort and safety of the patient.

For a tablet dispenser according to an embodiment of the invention the relevant information could be the number of dispensed tablets, the number of remaining tablets, the time of dispension and the type of dispensed tablets. The dispenser could store and/or communicate this information to an available unit of highest priority or other units within communication range.

In the following a preferred embodiment according to the invention is described in detail. This particular embodiment is meant as one example only of the invention and should not as such limit the scope of protection.

In the preferred embodiment a specific simple communication protocol has been chosen to simplify the explanation of the invention. In the chosen protocol a predefined apparatus is chosen as the unit of highest available priority (functional master module) which controls, coordinates and monitors the mutual data communication between all the apparatuses including itself. The master module collects or mirrors all the data stored in the other apparatuses. This collected or mirrored data can then be redistributed to the overall master module, any of the other apparatuses and/or an external unit (e.g. a personal computer or database system) for later retrieval and/or processing.

According to the invention the portable system can operate even if the overall master module is not present, since all the relevant apparatuses comprise internal storage means, so that they can store the relevant information when it is obtained and transmit it when they can reach the overall master module once again or transmit it, as described above, to the functional master module.

Preferably the information obtained is kept in the apparatuses so that the patient on request always can be presented with the latest measurements and/or information obtained or received.

A person skilled in the art could easily implement other communication protocols such as the ones described above.

In this embodiment a cap unit for a doser has been designated as the functional master module but any apparatus could have been chosen just as easily. Preferably, the master module will be the apparatus that the patient carries most often.

The invention will now be described in detail with reference to the FIGS. 1–12, in which FIG. 1 shows a prior art doser with a conventional cap;

Figure 1:
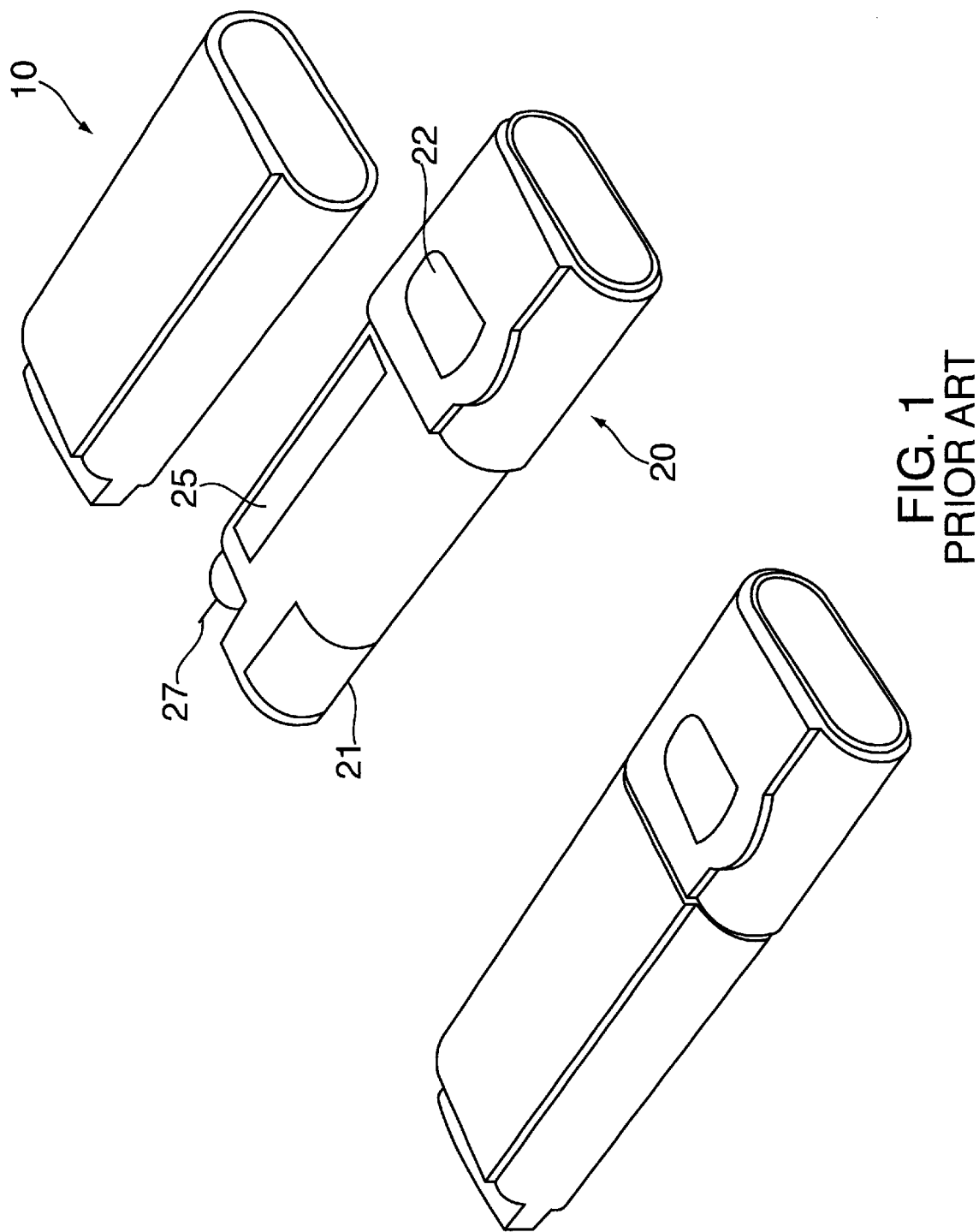

FIG. 1 shows a prior art doser 20 and a cap 10. The doser 20 comprises a turning wheel 21 for adjusting, either electronically or manually, the level/amount of medication to be administered, and a display 22 that shows the currently selected amount of medication to be administered. The doser 20 has processing means and storage facilities, like a CPU and RAM, for storing data, like the time, date and amount of medication of the last couple of administrations. This information can be shown in the display 22 at request. The doser 20 further comprises a cartridge (not shown) that contains the medication, and is fitted with a needle 27 through which the medication is administered. The doser 20 has a transparent window 25 so that the amount of medication left in the cartridge can readily be identified. The cap 10 can be fitted to the doser 20 so that one single compact unit and protection of the doser 20, needle 27, etc. are obtained.

Figure 2:
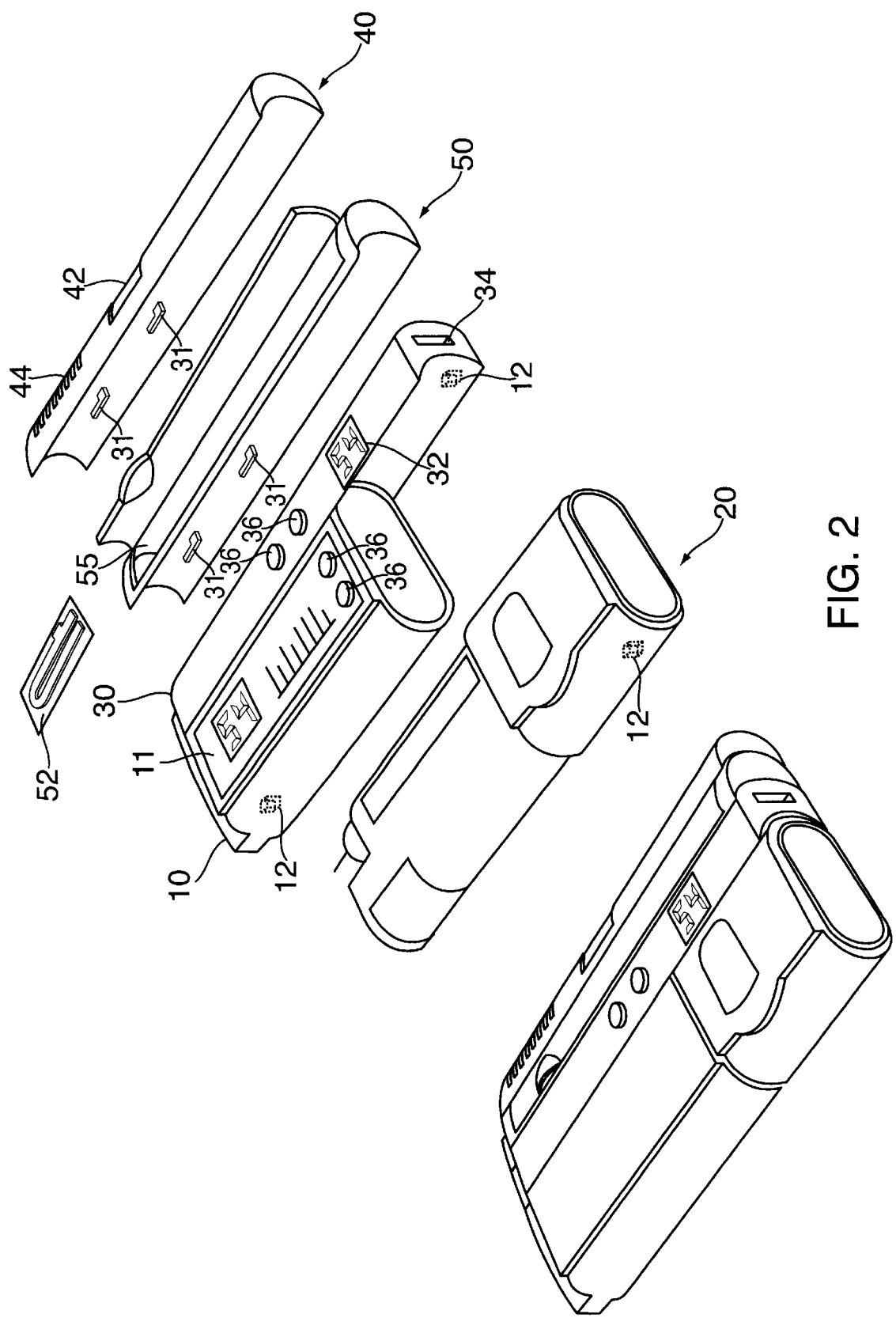
FIG. 2 shows a doser and a cap with a BGM, a lancet device and a container for test strips attached.

FIG. 2 shows a doser 20 with a cap 10 where the cap 10 is designated as the functional master module. The doser 20 corresponds to the doser 20 shown in FIG. 1 but with the additional feature of having transmitting, storing and receiving means 12 schematically shown. This enables the doser 20 to transmit the stored data, i.e., the time, date, amount and type of medication, to the functional master module 10 for storage and presentation there via the master module's receiving means. Information of the last couple of administration (time, date, type and amount of medication) can then easily be viewed on the display 11 on the master module. If the master module 10 is not present or active, e.g., if the user has turned it off or if has become broken, the doser 20 will just store the information locally or designate a new functional master module until the master module 10 becomes available and the patient will be able to view the information on the doser 20.

The doser 20 can also receive information via the receiving means 12 from the master module 10. This information could for instance be a predetermined amount of medication dictated remotely by a physician, an expert care-team or automatically e.g. according to a stored regime. The received information is then used to automatically set the correct amount of medication to be administered so that the patient does not have to worry about that aspect, which is a great advantage especially if the patient is a new user, elderly or handicapped.

Also shown is a BGM 30 which has means 34 for inserting test strips 52 containing a sample of blood, for analysis by the BGM 30 by operating the buttons 36. The result of the analysis is stored and either shown in the display 32 or transmitted to the master module 10 via the transmitting means 12 for storage and presentation on the larger display 11. The patient can at the same time be presented with the last couple of results over a time period.

A test strip container 50 is provided for the safe keeping/storing of test strips 52 in the space 55 and can be added/attached through locking means 31. With this addition, a test strip 52 will always be available.

Further shown is a lancet device 40 removably attached to the BGM 30 or the test strip container 50 by the locking means 31. This lancet device 40 is used by first loading the lancet device through the grip 44 and then pressing the button 42, which releases the lancet, piercing the skin, so that a blood sample can be obtained. With this inclusion, the lancet device 40 is always at hand. This has the advantage that a lancet device 40 is always available, for taking a blood sample and applying it to a test strip 52. The test strip 52 can then be inserted via the means 34 into the BGM 30, which will start analysing the blood sample and, after completion of the analysis, will show the result in the display 32. It is very useful to have the BGM 30 and the lancet device 40 attached together in one compact unit, since a BGM 30 would not normally be used without the lancet device 40, thereby avoiding the fuss and uncertainty of using multiple devices of perhaps different makes. On the other hand, if the user already has a lancet device and is accustomed to and familiar with the use of this particular lancet device, he can still use this original lancet device and just use the remaining items, which will be a compact set consisting of a doser 20 and a BGM 30 and if preferred the test strip container 50; The cost will be reduced hereby.

Figure 3:
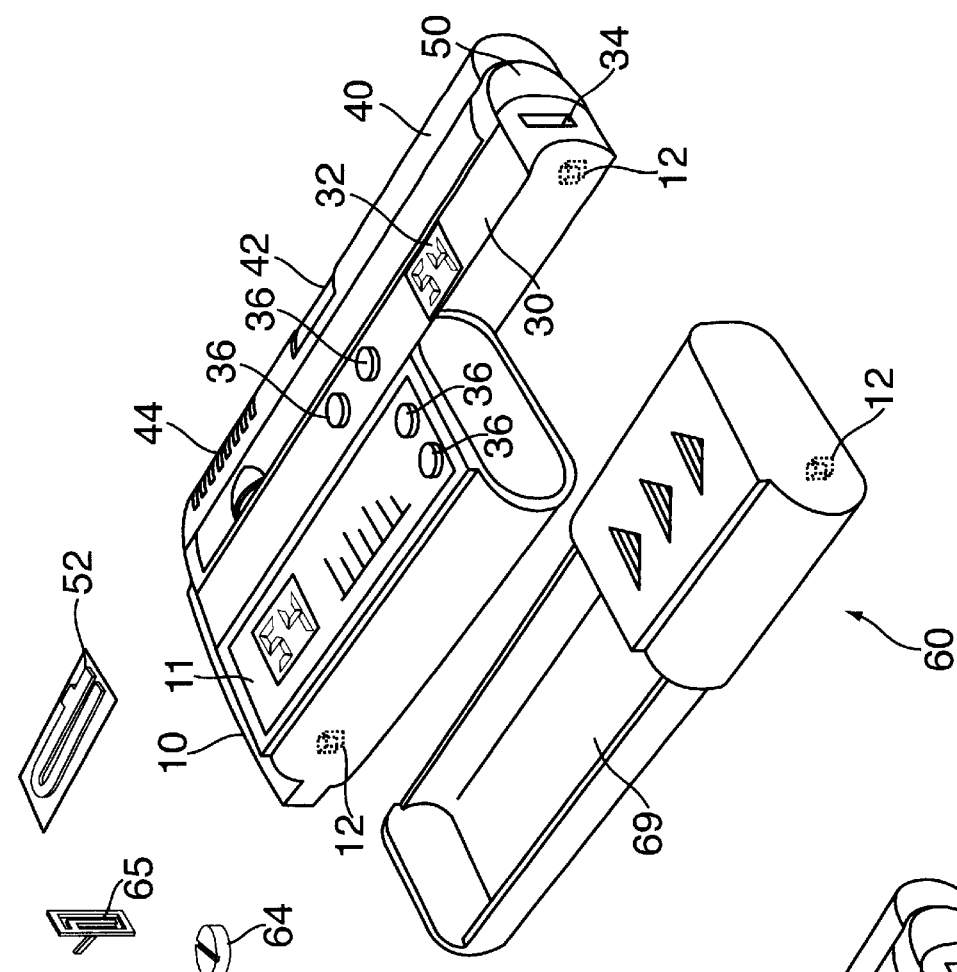
FIG. 3 shows a cap with a BGM, a lancet device, a test strip container attached and an additional container together with useful/needed extras.
Figure 3:
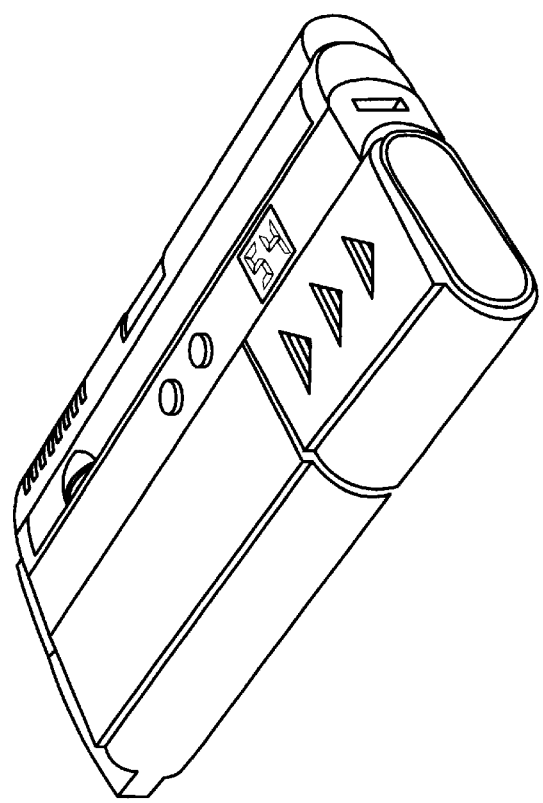

FIG. 3 shows the same units as are shown in FIG. 2, but instead of a doser 20, there is now provided a container unit 60 with a relative large space 69 for storing the items needed everyday for self-treatment. For a diabetic, e.g. such items could be a napkin 61 for wiping excessive blood after a sample has been taken, a waste container 62 for receiving used items, an extra cartridge 63 which could contain another type of insulin, spare needles 27 for the doser, spare lancets 65 for the lancet device 40, some glucose in the form of glucose tablets 64, etc. In some situations and in certain forms of diabetes, the injection of insulin may be replaced by administration of pills which may be stored in the container, which thus replaces the doser described previously. All these items, or the most relevant ones for a given situation, could be held in the container space 69 for easy retrieval, when needed.

The container unit 60 is provided with transmitting, receiving and storage means 12. These means are used to communicate an inventory list to the master module 10 on which the user can view and update the inventory list via the buttons 36.

This list could be transferred to an external unit (e.g. computer, laptop, palmtop, etc.) immediately or later, which could update a list of the patient's total holdings of objects, so that the system could notify the patient when he should order a new stock of objects. The ordering could also be done automatically by the system. In this way the patient will not have to be concerned whether he has all the necessary objects for a future span of time or not, which greatly improves the confidence and safety of the patient.

Figure 4:
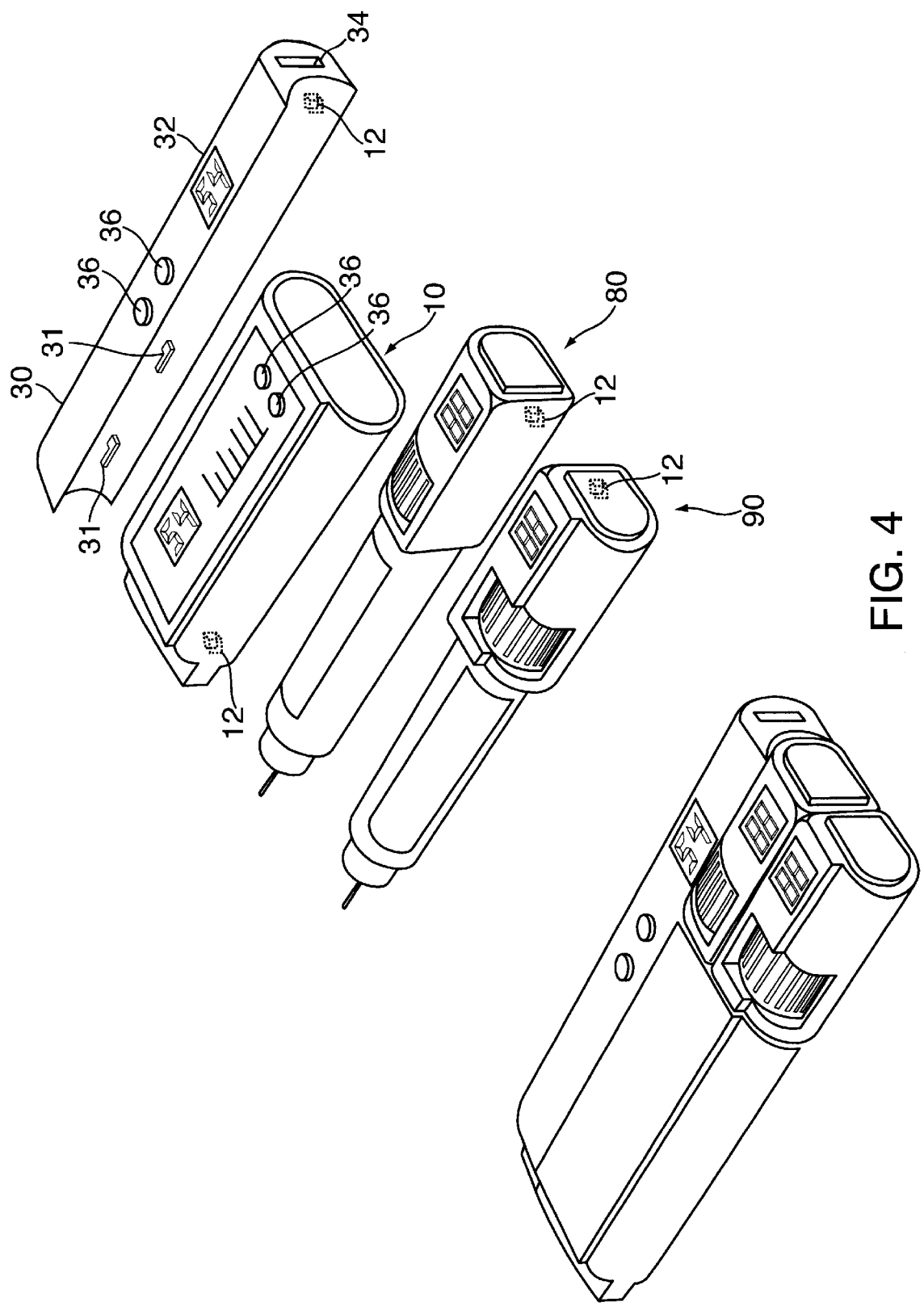
FIG. 4 shows a cap with a BGM and two dosers.

FIG. 4 shows a cap with a BGM and two dosers. The cap 10 and the BGM 30 correspond to the units described previously in connection with FIGS. 2–3. Also shown are two dosers 80, 90 of a smaller size than the doser 20 shown in FIGS. 2–3 but with a similar functionality.

The two dosers 80, 90 may contain two different kinds of insulin, e.g. fast and long acting insulin. In this way a user may have all the devices necessary ready at hand for a future span of time, e.g. for a weekend trip, etc., in a very compact form. The user may hereby administer the long acting insulin of one of the dosers 80, 90 to balance his glucose level on a larger time scale and use the BGM 30 on a regular basis to see if he needs any short acting insulin and administer it accordingly by using the other doser, which may provide a predetermined dose of medication on the basis of communication with the BGM 30 via their respective communications means 12.

Additionally, the individual dosers 80, 90 may communicate and exchange data with each other according to one of the protocols mentioned above, hereby mirroring their locally stored information, so that each unit belonging to the self-treatment system is aware of or at least capable of receiving information and state of the others. This also has the effect that only one of the dosers 80, 90 needs to exchange information with a unit responsible for the overall collection of information, e.g. located at the user's home.

Alternatively, the two dosers 80, 90 may be two dosers like the doser 20, each with their own cap 10, or be different in make, shape and/or color, e.g. a robust sports doser, etc. or one of the dosers 80, 90 may be a simpler spare doser/pan which is a simple mechanically operated pan but with communication, storing, processing and/or displaying means. The simpler pen may e.g. be brought along for a vacation if e.g. the accessibility of power for recharging is doubtful, since it uses less power, or just as a backup system.

In this way, a user may select the preferred doser for a given situation without having to worry about logging, updating, etc. of information, since the doser will automatically communicate with the other doser, other units and/or with the functional master module when these are within communication range and available.

Figure 5:
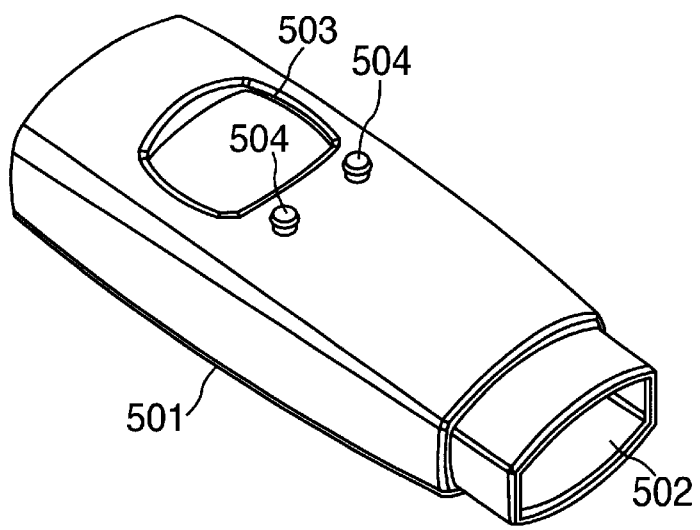
FIG. 5 shows an inhaler.

FIG. 5 shows an inhaler 501. The inhaler comprises a mouthpiece 502 for administering a predetermined dosage of medication to the patient. The predetermined dosage may either be specified by the patient via the buttons 504 or be set automatically from information received via receiving means (not shown) e.g. from the functional master module. Feedback like the dosage inhaled, and other relevant information like previous inhaled dosages and corresponding time stamp, etc. may be displayed to the patient on the display 503.

After inhalation information like the inhaled dosage may be stored locally and/or transmitted to e.g. the functional master module by storing and transmitting means (not shown), respectively.

Figure 6:
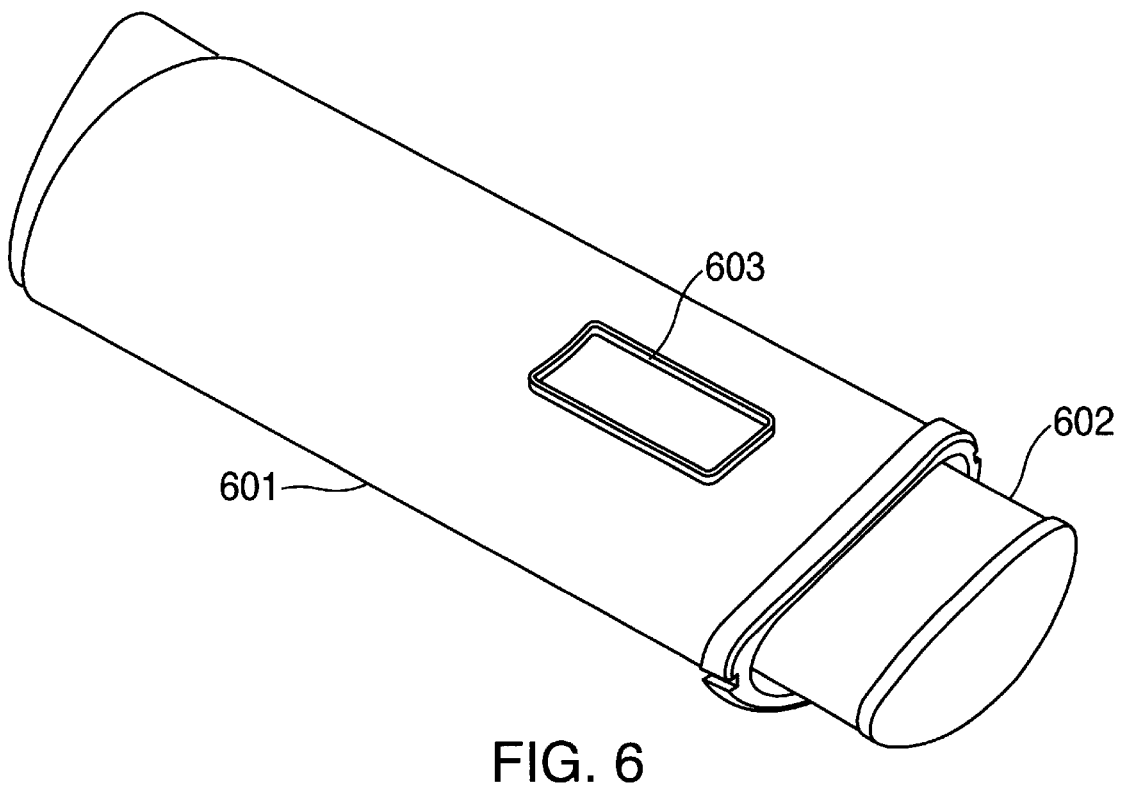
FIG. 6 shows a tablet dispenser.

FIG. 6 shows a tablet dispenser 601. The tablet dispenser 601 is used to administer a tablet of medication to a patient e.g. in order to regulate the glucose level for a diabetes patient. Other tablet dispensers containing different types of medication may also be included in the system. For tablet dispenser 601 is preferably operated by a single large button 602, thereby making the administration of medication very easy and secure.

After administering a tablet information may be displayed at the display 603 together with other relevant information and feedback to the patient. The type and amount of tablets dispensed may also be stored and/or transmitted to e.g. the functional master module by storing and transmitting means (not shown), respectively.

Information like recommended type and amount of medication to be dispensed may also be received via receiving means (not shown). If the type of the loaded tablets is known to the system a check if the type complies with the recommended type may be made and a warning may be issued if the check fails.

Figure 7:
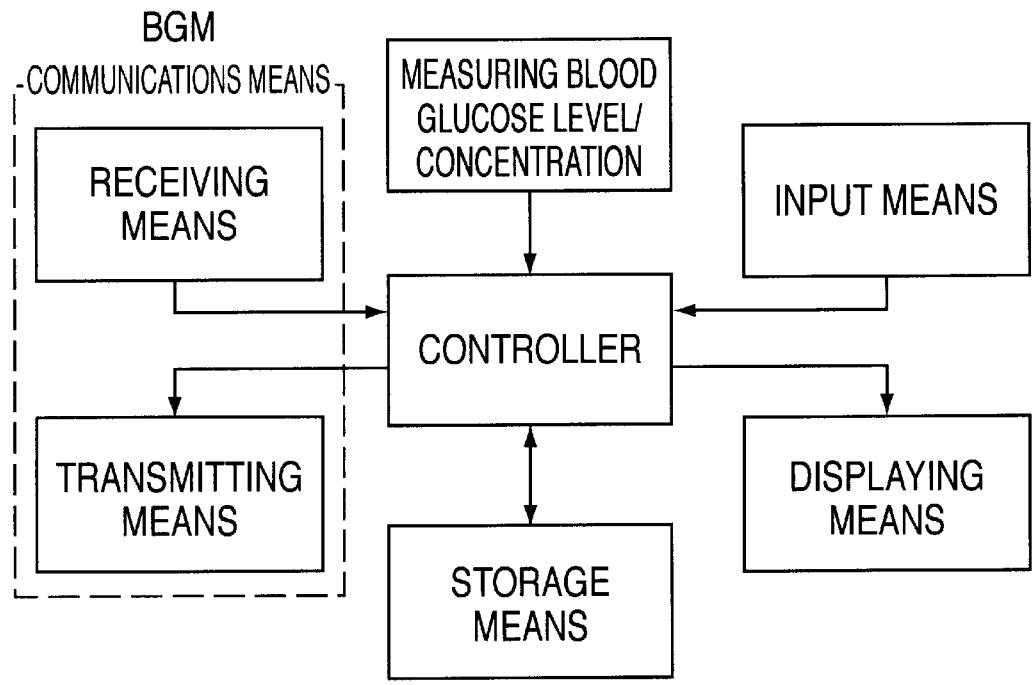
FIG. 7 shows a schematic functional diagram of a BGM according to an embodiment of the invention.

FIG. 7 shows a schematic functional diagram of a BGM according to an embodiment of the invention. The BGM consists of the following functional blocks: 'Controller', 'Receiving means', 'Transmitting means', 'Storage means', 'Displaying means', 'Input means', and 'Measuring Blood Glucose Level/Concentration'.

The central block is the functional block 'Controller' which coordinates, monitors and controls the tasks of all the other functional blocks as well as process information. The 'Receiving means' and 'Transmitting means' is responsible for receiving and transmitting of information data, respectively. The block 'Measuring Blood Glucose Level/Concentration' performs the measurement of the blood glucose level/concentration on e.g. a test strip, containing a blood sample. The 'Displaying means' can display relevant information to the patient e.g. the result of a measurement and a time stamp containing the time and date of the measurement. The result of the measurement can be stored in the 'Storage means' for later retrieval and further be sent to another apparatus (e.g. the functional master module) through the 'Transmitting means'. All these tasks take place under the supervision and coordination of the 'Controller' block.

The BGM according to an embodiment of the invention could thus be operated in the following way. When a request for a measurement of the blood glucose level/concentration is made either by the patient through the 'Input means' or by another apparatus through the 'Receiving means', the controller receives the request and activates the 'Measuring Blood Glucose Level/Concentration' block, which initiates and performs the measurement of the blood glucose level when the patient inserts a test strip with a sample of blood into a slot on the apparatus. Previously a calibration of the measurement equipment could be made by insertion of a calibration test-strip. The result and a time stamp of the measurement are then transferred to the storage means, and the controller can send the result via the transmitting means to another device preferably the functional master module if it is active and within range.

All these functional blocks could be implemented by prior art/standard components. The block labeled 'Controller' could e.g. be implemented by any type of CPU, micro processor, micro controller, EEPROM or ROM containing software, firmware, etc. The functional block 'Storage means' could be standard RAM.

The BGM is only an example of an apparatus that could be used according to this invention. Any other body fluid analyser e.g. lipid monitor or the like could be used.

Figure 8:
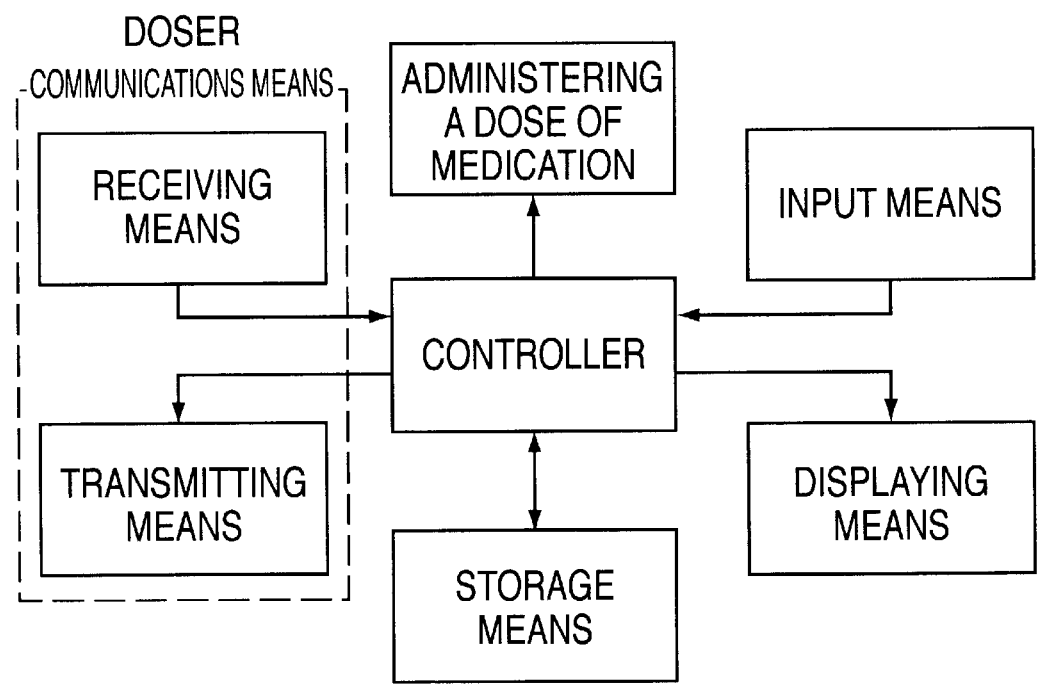
FIG. 8 shows a schematic functional diagram of a doser according to an embodiment of the invention.

FIG. 8 shows a schematic functional diagram of a doser according to an embodiment of the invention. The doser consists of the following functional blocks: 'Controller', 'Receiving means', 'Transmitting means', 'Storage means', 'Displaying means', 'Input means' and 'Administering a dose of Medication'. These functional blocks correspond to the blocks previously described for the BGM in FIG. 7, except for the block 'Administering a dose of Medication', and will therefore not be explained once more.

The functional block 'Administering a dose of Medication' administers a dose of medication e.g. insulin. The amount of medication could be set by the patient through the 'Input means' or be set electromechanically by the 'Controller' block according to information received via the 'Receiving means'. This information could be prescribed by a physician, by an expert care-team or automatically, so that elderly or handicapped people would only have to activate the doser through the input means to be administered a dose of medication. After the activation of the doser, information e.g. type of medication (e.g. long acting or short acting insulin), amount of medication and the corresponding time stamp (date and time) is stored in the 'Storage means' and transmitted to an apparatus (preferably the functional master module).

Other drug administration devices than an insulin doser could be used in accordance with the invention. These could e.g. be an electronic inhaler, tablet dispensers, devices that administer growth hormones, etc. One could also have an device that obtains information of orally obtained medication like OHA (Oral Hyperglychemical Agent). This would, however, require the user to manually input the type and amount of medication, which could be done by choosing icons, selecting an object in a predetermined list or typing the information by alphanumeric keys. Preferably, a predetermined list would require the user to just enter (e.g. by icons or alphanumeric keys) the relevant text once and then later just present the user with the already entered text and only ask for the amount and type (which could also be pre-entered in the same fashion).

Figure 9:
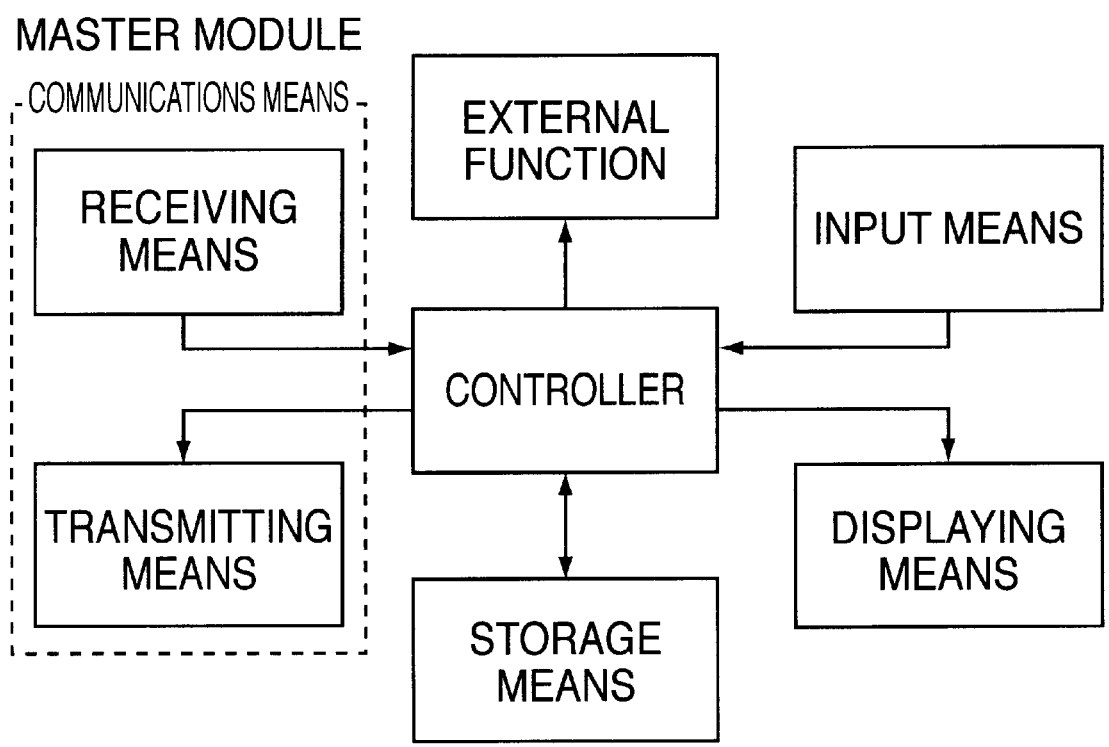
FIG. 9 shows a schematic functional diagram of a unit of highest priority (functional master module) according to an embodiment of the invention.

FIG. 9 shows a schematic functional diagram of a functional master module according to an embodiment of the invention. The master module consists of the following functional blocks: 'Controller', 'Receiving means', 'Transmitting means', 'Storage means', 'Displaying means', 'Input means' and 'External function'. These functional blocks correspond to the blocks previously described with reference to FIGS. 7 and 8, except for the block 'External function', and will therefore not be explained once more.

The functional master module is the module responsible for the coordination, supervision and control of the information and data exchange between itself and all the other present and activated apparatuses. These apparatuses identify themselves to the master module when they are within range so that the master module always knows which apparatuses are present and activated. The master module also receives and stores all the information and data generated in the individual apparatuses for later retrieval and/or transmission to an external unit/system (e.g. computer or database) e.g. via a specific unit for further storage and processing. The relevant information can be displayed on the larger display of the master module and be acted upon by the patient.

Some of the tasks of the master module could be implemented in the external unit and vice versa.

The master module could be any of the apparatuses as represented by the functional block 'External function' in FIG. 9, but is in this embodiment the cap unit 10 shown in FIGS. 2–4, and has as such no external function. Other functions may readily be implemented in this stock.

Figure 10A:
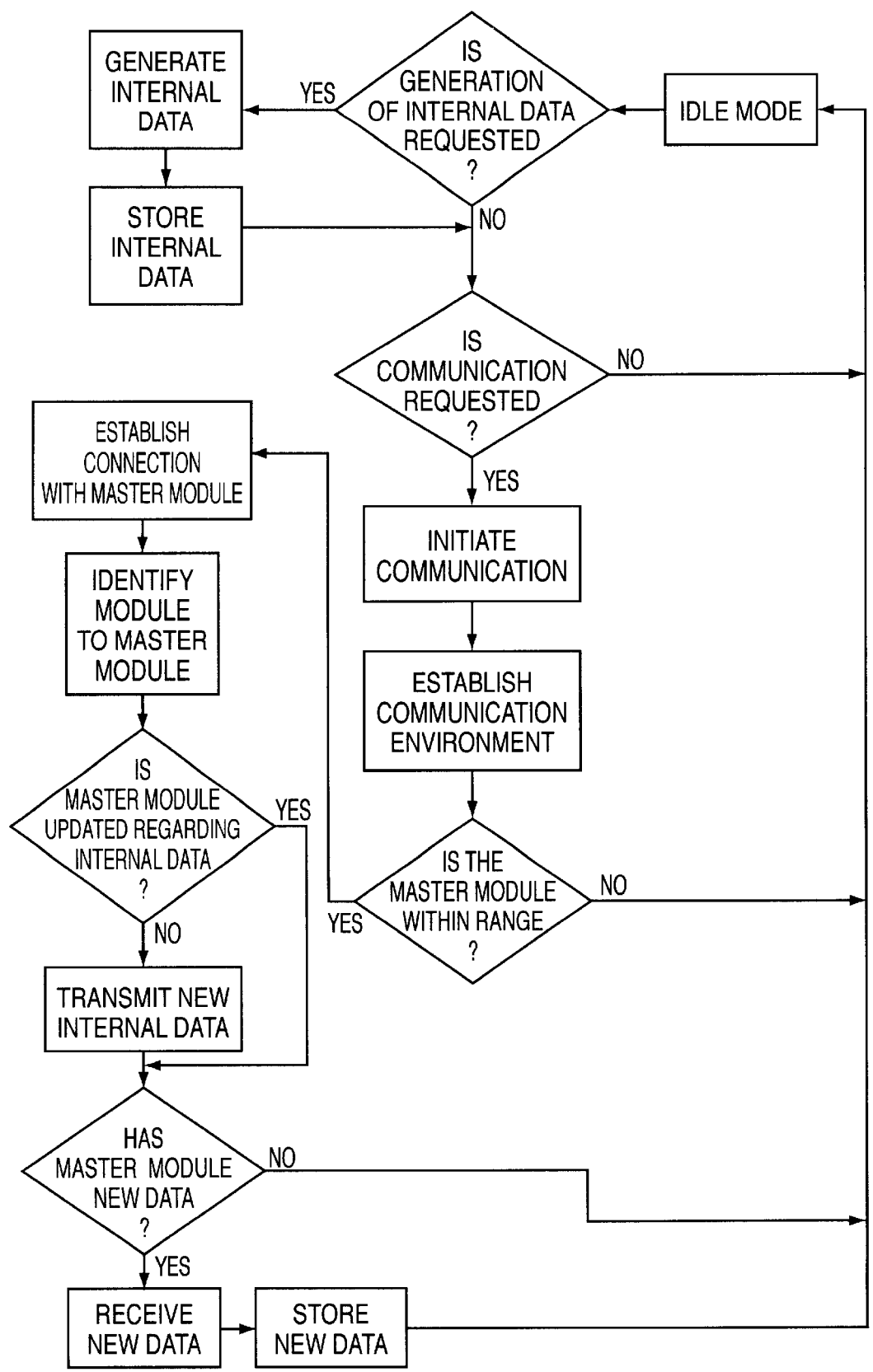
FIG. 10a shows a flowchart illustrating an apparatus generating new data (e.g. a BGM) and how the apparatus behaves with respect to data generation and communication according to one aspect of the invention.

FIG. 10a shows a flowchart illustrating an apparatus generating new data (e.g. a BGM) and how the apparatus behaves with respect to data generation and communication.

In idle mode the apparatus determines whether or not data generation is requested. If this is the case (e.g. if the user has inserted a blood glucose measuring strip into the apparatus), the data generation block assumes priority and completes the procedures associated with the data generation (e.g. measurement of the blood glucose concentration). After completion of the data generation the data is stored in the internal memory of the apparatus.

After completion of the data generation or after determination that data generation was not requested, the apparatus determines whether or not communication is requested—either by the apparatus itself (several criteria can issue the communication request e.g. a timing event, a user interface event, etc.) or by an apparatus different from the apparatus itself (e.g. a request from the functional master module). If communication is not requested, the apparatus resumes its idle mode. If communication is requested, the apparatus sends out a request for the other apparatuses within its range to identify themselves to the apparatus—enabling it to establish the present communication environment. Based on the established communication environment the apparatus identifies whether or not the functional master module is within range of the apparatus and active. If the master module is not within range of the apparatus, the communication is terminated and the apparatus returns to its idle mode. If however, the master module is within range of the apparatus, the apparatus sets up a connection with the master module and identifies itself to the master module. After exchange of apparatus identification it is established whether the master module is updated with respect to the internal data contained in the internal memory of the apparatus or not. If the master module is updated, the data is not transmitted once more. If, however, the master is not updated regarding the internal data of the apparatus, the data necessary to update the master is transmitted from the apparatus to the master module. After completion of the data transmission it is likewise established if the master module contains data relevant to the apparatus which is not present in the apparatus. If this is the case, the master module transmits the relevant data to the receiving means of the apparatus after which the data is stored in the internal memory of the apparatus. After storage of the received data or if no data transmission was necessary, the apparatus returns to its idle mode and the circle is completed.

Figure 10B:
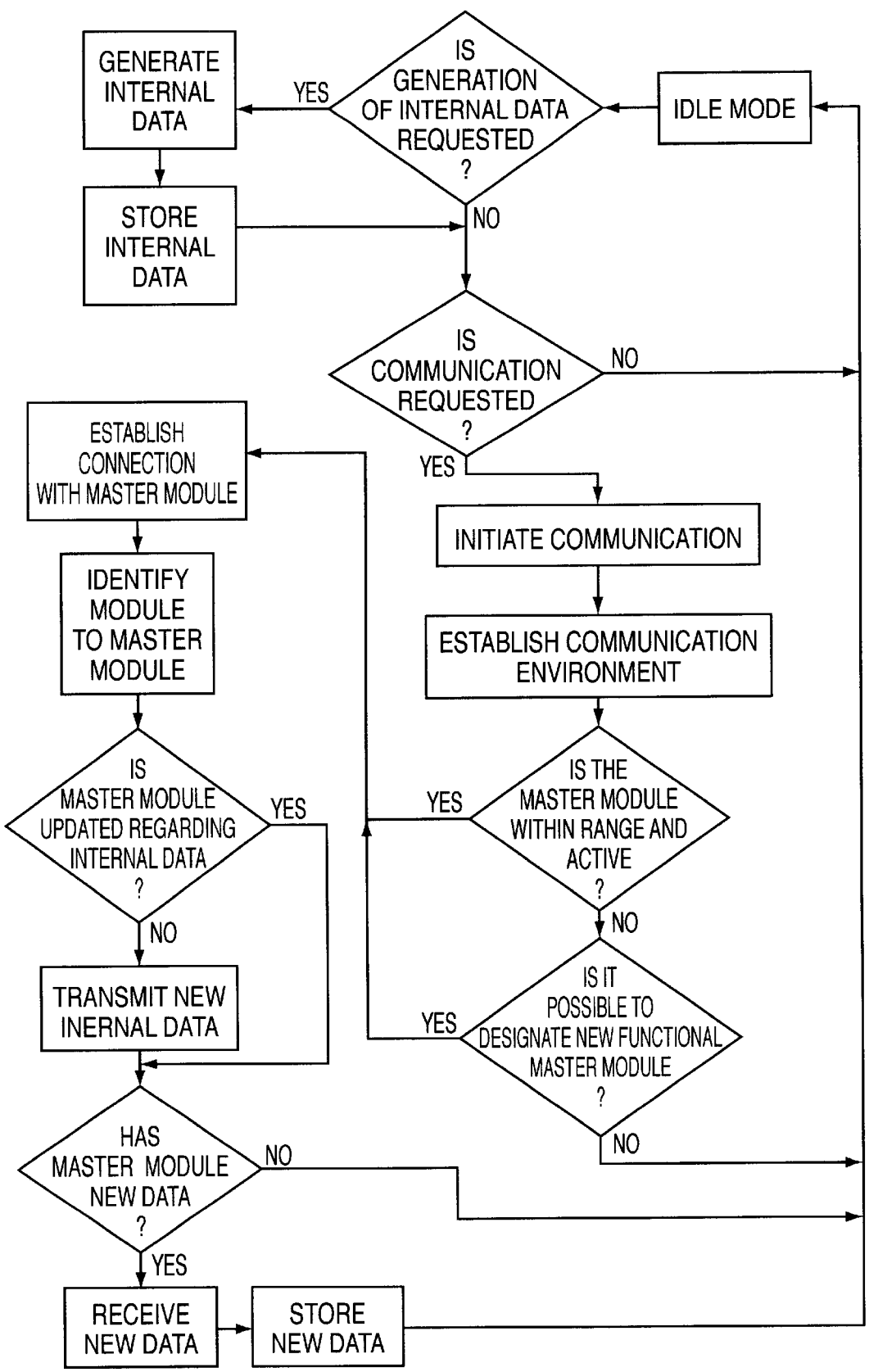
FIG. 10b shows a flowchart illustrating an apparatus generating new data (e.g. a BGM) and how the apparatus behaves with respect to data generation and communication according to another aspect of the invention.

FIG. 10b shows a flowchart illustrating an apparatus generating new data (e.g. a BGM) and how the apparatus behaves with respect to data generation and communication according to another aspect of the invention. This flowchart corresponds to the one shown in FIG. 10a with the exception that failing to reach the master module leads to that a check whether it is possible to designate a new functional maser module is made.

If the check whether it is possible to designate a new functional master module also fails the apparatus returns to its idle mode, and if a new functional master module can be designated a connection with the newly designated master module is established.

Figure 11:
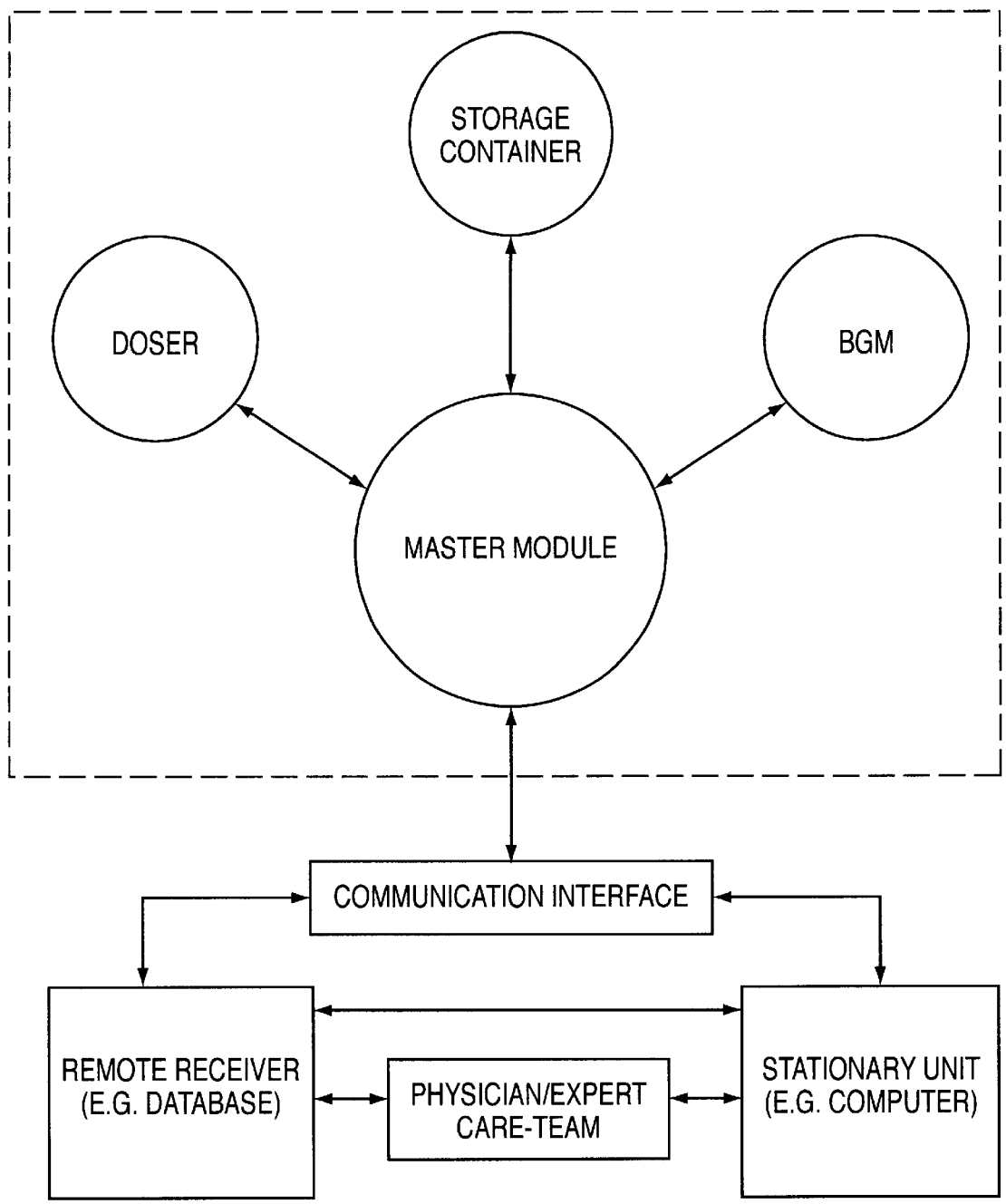
FIG. 11 illustrates the general concept according to an embodiment of the invention with respect to communication.

FIG. 11 illustrates the general concept according to an embodiment of the invention with respect to communication. Here the system consists of the exemplary portable units: a functional master module, a doser, a BGM, the remote units: Remote Receiver, Physician/Expert Care-team and Stationary Unit and a Communication Interface between them. The functional master module could e.g. be another doser, an inhaler, etc.

The master module controls the information and data flow between itself and the other apparatuses and collects relevant data and information from all the other portable units. This data and information could e.g. be amount of medication, type of medication, body fluid concentration, time stamp (date and time) and inventory logistics. Additionally, the patient can manually input information and data related to amount of food, measurement of physical activity in the way described above. This data and information can then be transmitted via a communication interface (which may be built into the master module) to external units like a database for data acquisition of the patient's data over time or a computer which the patient uses to be kept informed about his treatment. Alternatively, all the apparatuses could communicate to all the others.

If the functional master module becomes unavailable a new functional master module may be designated among the rest of the active apparatuses.

The information in the database can be accessed by a physician or an expert care-team who could easily and quickly check for compliance to e.g. a diet or treatment course/progress. The physician or expert care-team could send a notification (e.g. alert or warning) to the patient if the data shows an inappropriate future treatment span. The patient could also be notified of a future appointment in this way or receive guidance.

The system also makes it possible for the physician or expert care-team to give the patient a number of choices to a given situation. The patient could e.g. be informed that the blood glucose level/concentration is quite high and the patient could be presented with the choices of either exercising for given amount of time or administering a given amount of a given type of medication. The possibility of choices makes the patient feel more in control of the treatment and enhances the therapeutic value of the treatment. This could also be done automatically be the system.

Many of the above tasks could be fully automated by utilization of an expert system which is fully updated with the patient's data and condition and has access to the patient's behavior over time.

Figure 12:
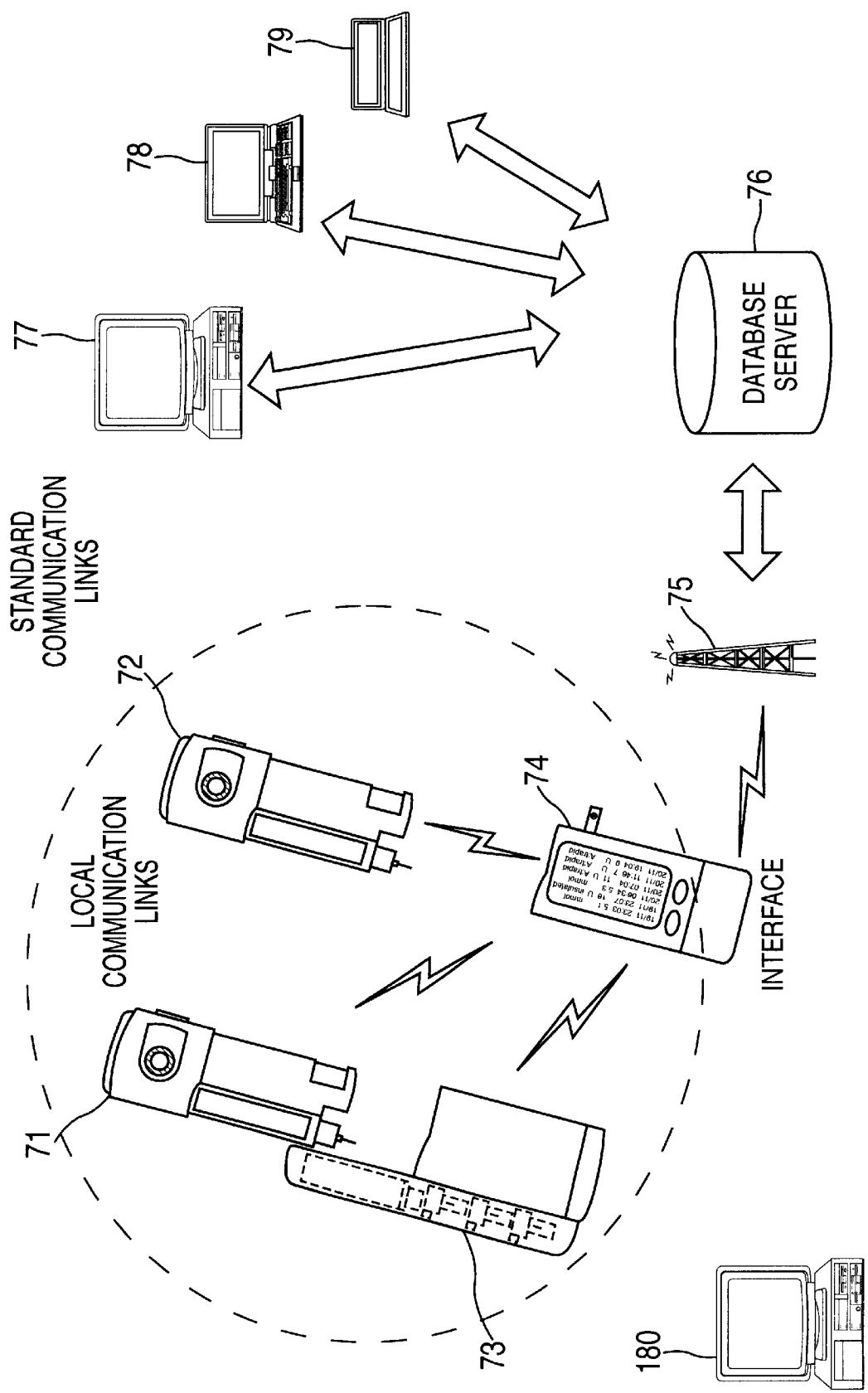
FIG. 12 illustrates two dosers and their communication paths.

FIG. 12 illustrates two dosers and their communication paths The dosers are identical for the typical patient, one doser containing fast acting insulin, the other doser containing long acting insulin. The dosers comprise a micro controller and memory as shown in FIG. 8. The dosers are capable of holding information about the insulin type they contain. This information may either be obtained by the doser reading e.g. a bar code on the cartridge or the information may be input from the patient. Thus the features of the doser enable it to log information about the insulin treatment (insulin type size of the dose and time stamp)

One doser is equipped with a cap unit 73 which acts as a storage container for an extra insulin cartridge, needles etc. The storage container is capable of keeping track of the contents of the container which enables it to keep the inventory list updated, as described earlier in the present document.

The other doser is equipped with a cap unit 74 comprising a BGM, a micro controller and memory. This enables the cap unit 74 to log information about the blood glucose concentration (with time stamp).

All the dosers 71, 72 and the cap units, 73, 74 comprise an interface which enables them to exchange data. In the present example, the functional master module is the BGM cap until 74 which, in addition to the local interface, comprises an interface that enables it to communicate with external units through standard communication links (RS-232, wireless local area network, phone, cellular phone, pager, satellite link, etc.). Through these communication links, the patient's treatment data can be transferred to the patient's own computer 180 or via, e.g., the telephone system 75 to the patient's electronic medical record on a central server 76. From here, the treatment data may be accessed by the patient, e.g., from a web page, using a stationary computer 77, a laptop computer 78, a handheld computer 79, etc. Apart from the patient, the care team can access the patient's treatment data. The patient's master unit 74 can receive data from the central server 76, in addition to the transmitting data.

This system has the advantage that the system can function on 3 levels:
If one of the patient's devices 71, 72, 73, 74 is isolated by means of communication, it will log data.
When the patient's devices 71, 72, 73, 74 are within communication distance, the treatment data are transferred to the master unit 74, enabling it to supply the patient with a overview of his treatment as well as warnings of alarms if data shows that a potential dangerous situation may occur. When the master device 74 is connected to the central server 76 through standard communication links, the treatment data is transferred to the patient's electronic medical record. This enables an expert system on the central server to notify the care team if needed. The care team may send information back to the user or send help if needed.

Furthermore it is well known that due to the safety of the patient, the development of a medical device is a time consuming task. Using a local communication form between the patient's devices 71, 72, 73, 74 has the advantage that only the master device 74 need to be redesigned to keep up with the continuous change in the standard communication links.

What is claimed is:

1. A medical system comprising a plurality of portable apparatuses for use by a patient for medical self-treatment, the treatment including a first operation and at least a second operation, the system comprising a first apparatus for performing the first operation and a second apparatus for performing the second operation, each of said first and second apparatuses comprising a means for storing, processing and/or displaying information and a means for transmitting and receiving of information so that each apparatus is able to exchange data with said other apparatus, wherein
   (a) either said first or said second apparatus can function as a potential functional master module;
   (b) one of said potential functional master modules is dynamically designated as the functional master module, and
   (c) said functional master module is adapted to control an attempted data communication, initiated on request, between said apparatuses and is adapted to receive and store relevant information generated in at least one of the apparatuses, and
wherein said apparatuses are selected from the group consisting of:
   a lancet device,
   a body fluid analyzer,
   a drug administration system for administering a predetermined dose of medication to the patient, and
   a sensor for obtaining body characteristics.

2. A medical system according to claim 1, wherein both said means are preadjusted to handle a common set of measuring and information representations and wherein said common set of measuring and information representations comprises blood glucose concentrations.

3. A medical system according to claim 1, wherein said body fluid analyser is a blood glucose monitor.

4. A medical system according to claim 3, wherein said blood glucose monitor comprises storing, transmitting, and/or displaying means for blood glucose level and/or time stamp.

5. A medical system according to claim 1, wherein said body fluid analyser is a liquid monitor.

6. A medical system according to claim 1, wherein both said means are preadjusted to handle a common set of measuring and information representations and wherein said common set of measuring said information representations comprises body weight and blood pressure.

7. A medical system according to claim 1, wherein said drug administration system is selected from the group of:
   an insulin injecting device;
   an inhaler; and
   a tablet dispenser.

8. A medical system according to claim 7, wherein said insulin injecting device comprises storing, transmitting, receiving and/or displaying means for a number of units of medication, type of medication and/or time stamp.

9. A medical system according to claim 1, wherein said apparatus has one or more storage containers for storing a supply of one or more of the following:
   a supply of lancets;
   a supply of test strips;
   an extra supply of insulin; and
   a supply of needles.

10. A medical system according to claim 9, wherein said one or more storage containers comprises storing, transmitting, receiving, and/or displaying means for inventory logistics.

11. A medical system as recited in claim 1, wherein said first and second apparatuses are the same type of apparatus.

12. The medical system of claim 11, wherein said first and second apparatuses are both drug administration units.

13. The medical system of claim 12, further comprising a body fluid analyser.

14. A medical system comprising a plurality of portable apparatuses for use by a patient for medical self-treatment, the treatment including a first operation and at least a second operation, the system comprising a first apparatus for performing the first operation and a second apparatus for performing the second operation, each of said first and second apparatuses comprising a means for storing, processing and/or displaying information and a means for transmitting and receiving of information so that each apparatus is able to exchange data with said other apparatus, wherein (d) either said first or said second apparatus can function as a potential functional master module;

(e) one of said potential functional master modules is dynamically designated as the functional master module, and (f) said functional master module is adapted to control an attempted data communication, initiated on request, between said apparatuses and is adapted to receive and store relevant information generated in at least one of the apparatuses, and wherein said apparatuses are selected from the group of:

a lancet device, a body fluid analyzer, a drug administration system for administering a predetermined dose of medication to the patient, and a sensor for obtaining body characteristics;

and wherein said system comprises a means for presentation of choices to the patient for a given situation, said presentation being dependent on said patients previous choices.

15. A method of controlling data information between a plurality of portable apparatuses for use by a patient for medical self-treatment, the treatment including a first operation and at least a second operation, said plurality of apparatuses comprising a first apparatus for performing the first operation, and at least a second apparatus for performing the second operation, each of said first and second apparatuses comprising a means for storing, processing and/or displaying information for transmitting and receiving of information and a means so that each apparatus is able to exchange date with said other apparatus, wherein the method comprises the steps of:

(a) dynamically designating a single apparatus as a functional maser module among said at least two apparatuses;

(b) initiating an attempted data communication between said apparatuses on request, said communication being controlled by said functional master module;

(c) receiving and storing in said functional master module relevant information generated in said other apparatus;

and wherein the apparatuses are selected from the group of:

at least one lancet device;

at least one body fluid analyzer;

at least one drug administration system for administering a predetermined dose of medication to the patient; and at least one sensor for obtaining body characteristics.

* * * * *

UNITED STATES PATENT AND TRADEMARK OFFICE
CERTIFICATE OF CORRECTION

PATENT NO. : 6,540,672 B1
APPLICATION NO. : 09/450193
DATED : April 1, 2003
INVENTOR(S) : Jan Henning Simonsen et al.

It is certified that error appears in the above-identified patent and that said Letters Patent is hereby corrected as shown below:

Title Pg, Item (74), under "Attorney, Agent, or Firm," please delete "Richard W. Bosk, Esq." and insert therefor --Richard W. Bork, Esq.--

Title Pg, Item (57), under "ABSTRACT," line 1, please delete "This invention relates to an system for self treatment." and insert therefor --This invention relates to a system for self treatment.--

In the claims, column 16, line 10, please delete "maser" and insert therefor --master--.

Signed and Sealed this

Third Day of August, 2010

David J. Kappos
*Director of the United States Patent and Trademark Office*